United States Patent
Lamey et al.

(10) Patent No.: US 7,538,087 B2
(45) Date of Patent: May 26, 2009

(54) AGENT AGAINST PERIODONTAL DISEASE

(75) Inventors: Philip-John Lamey, 19 Dalchoolin, Circular Road, Cultra, Hollywood, County Down BT18 0HR (GB); Fionnuala Teresa Lundy, Belfast (GB); Christopher Shaw, Comber (GB)

(73) Assignee: Philip-John Lamey, Holywood (GB)

( * ) Notice: Subject to any disclaimer, the term of this patent is extended or adjusted under 35 U.S.C. 154(b) by 357 days.

(21) Appl. No.: 10/257,777

(22) PCT Filed: Apr. 17, 2001

(86) PCT No.: PCT/GB01/01843

§ 371 (c)(1), (2), (4) Date: Apr. 8, 2003

(87) PCT Pub. No.: WO01/79297

PCT Pub. Date: Oct. 25, 2001

(65) Prior Publication Data

US 2004/0185012 A1  Sep. 23, 2004

(30) Foreign Application Priority Data

Apr. 14, 2000 (GB) ................................. 0009124.9

(51) Int. Cl.
A61K 38/16 (2006.01)
(52) U.S. Cl. .................. 514/12; 530/324; 601/162; D28/65; 106/35
(58) Field of Classification Search ........................ None
See application file for complete search history.

(56) References Cited

U.S. PATENT DOCUMENTS 5,688,766 A * 11/1997 Revis .......................... 514/12

FOREIGN PATENT DOCUMENTS

WO 94/15578 7/1994
WO WO 94/15578 * 7/1994
WO 00/08159 2/2000

OTHER PUBLICATIONS

Lehner, Journal of the Royal Society of Medicine, 1978, 71, 161-163.*
Abe, et al., J Dent Res., 10998, 77(11), 1913-1919.*
Baron, et al., 1999, Journal of Peridontal Research, 34(8), 437-444.*
JADA, 2001, 132, 1339.*
Baron, et al., 1999, J Periodont Res., 34, 437-444.*
Henskens, et al., 1993, J Periodont Res., 28, 43-48.*
Loesche, Infectious Disease Clinics of North America, 2007, vol. 21, Issue 2, 1 Page (abstract).*
Abe, et al., J Dent Res., 1998, 77(11), 1913-1919.(reference cited on PTO-892 of office action dated Oct. 30, 2006 and the year of publication was erroneously listed).*
Libuse, et al: "Cystatins-inhibitors of cysteine proteinases" *Critical Reviews in Oral Biology and Medicine*, vol. 3, No. 4, pp. 307-332 (1992).
Vanden, Abbelle A., "Le role antiseptique de la salive," *Rev. Belge Med. Dent.*, pp. 52-58, 1992. (English summary only).

* cited by examiner

*Primary Examiner*—Andrew D Kosar
*Assistant Examiner*—Satyanarayana R Gudibande
(74) *Attorney, Agent, or Firm*—Daniel A. Monaco; Drinker Biddle & Reath LLP

(57) ABSTRACT

The present invention relates to a product for preventing periodontal disease wherein the product includes or is based on a Cystatin type peptide. The invention also relates to dentifrice preparations including Cystatin and to medicaments including Cystatin for the treatment or prevention of periodontal disease and to the use of a nucleic acid sequence which encodes a Cystatin type peptide.

2 Claims, 1 Drawing Sheet

Figure 1: 141 Amino Acid Sequence of Cystatin Molecule

Met Ala Gln His Leu Ser Thr Leu Leu Leu Leu Ala Thr Leu Ala
 1            5              10              15

Val Ala Leu Ala Trp Ser Pro Lys Glu Glu Asp Arg Ile Ile Pro Gly
         20              25              30

Gly Ile Tyr Asn Ala Asp Leu Asn Asp Glu Trp Val Gln Arg Ala Leu
         35              40              45

His Phe Ala Ile Ser Glu Tyr Asn Lys Ala Thr Lys Asp Asp Tyr Tyr
     50              55              60

Arg Arg Pro Leu Arg Val Leu Arg Ala Arg Gln Gln Thr Val Gly Gly
 65              70              75              80

Val Asn Tyr Phe Phe Asp Val Glu Val Gly Arg Thr Ile Cys Thr Lys
             85              90              95

Ser Gln Pro Asn Leu Asp Thr Cys Ala Phe His Glu Gln Pro Glu Leu
         100             105             110

Gln Lys Lys Gln Leu Cys Ser Phe Glu Ile Tyr Glu Val Pro Trp Glu
     115             120             125

Asn Arg Arg Ser Leu Val Lys Ser Arg Cys Gln Glu Ser
     130             135             140

Molecular Weight: 16361 Da

```
                         SEQUENCE LISTING

<160> NUMBER OF SEQ ID NOS: 2

<210> SEQ ID NO 1
<211> LENGTH: 28
<212> TYPE: PRT
<213> ORGANISM: Artificial
<220> FEATURE:
<223> OTHER INFORMATION: Chemically synthesized cystatin type peptide

<400> SEQUENCE: 1

Ile Ile Pro Gly Gly Ile Tyr Asn Ala Asp Leu Asn Asp Glu Trp Val
1               5                   10                  15

Gln Arg Ala Leu His Phe Ala Ile Ser Glu Tyr Asn
            20                  25

<210> SEQ ID NO 2
<211> LENGTH: 141
<212> TYPE: PRT
<213> ORGANISM: Homo sapiens

<400> SEQUENCE: 2

Met Ala Gln His Leu Ser Thr Leu Leu Leu Leu Leu Ala Thr Leu Ala
1               5                   10                  15

Val Ala Leu Ala Trp Ser Pro Lys Glu Glu Asp Arg Ile Ile Pro Gly
            20                  25                  30

Gly Ile Tyr Asn Ala Asp Leu Asn Asp Glu Trp Val Gln Arg Ala Leu
        35                  40                  45

His Phe Ala Ile Ser Glu Tyr Asn Lys Ala Thr Lys Asp Asp Tyr Tyr
    50                  55                  60

Arg Arg Pro Leu Arg Val Leu Arg Ala Arg Gln Gln Thr Val Gly Gly
65                  70                  75                  80

Val Asn Tyr Phe Phe Asp Val Glu Val Gly Arg Thr Ile Cys Thr Lys
                85                  90                  95
```

```
-continued

Ser Gln Pro Asn Leu Asp Thr Cys Ala Phe His Glu Gln Pro Glu Leu
            100                 105                 110

Gln Lys Lys Gln Leu Cys Ser Phe Glu Ile Tyr Glu Val Pro Trp Glu
            115                 120                 125

Asn Arg Arg Ser Leu Val Lys Ser Arg Cys Gln Glu Ser
            130             135             140
```

AGENT AGAINST PERIODONTAL DISEASE

The present invention relates to a method of preventing periodontal disease. More specifically a peptide is disclosed which is shown to have a novel effect in respect of its antimicrobial activity against periodontal pathogens.

Periodontal disease is recognised in infection with a number of pathogens identified but the exact significance of each remains to be clarified. Nevertheless it is undoubtedly an infective process and surprisingly for an infective process is currently treated by mechanical means involving tooth brushing, scaling, polishing and the use of dentifrice. Some dentifrice contain substances which are claimed to be beneficial in reducing gingivitis and periodontal disease.

It is an object of the present invention to provide a product for preventing periodontal disease.

According to the present invention there is provided a product for preventing periodontal disease, the product including a Cystatin type peptide or a natural or synthetic peptide which is similar to or based on the sequence of a Cystatin type peptide.

Preferably the peptide is or is based on Cystatin SN.

The invention also provides dentifrice preparations incorporating a Cystatin type peptide or a natural or synthetic peptide which is similar to or based on the sequence of a Cystatin type peptide.

Preferably said Cystatin peptide will include at least 60% of the amino acid sequence: I I P G G I Y N A D L N D E W V Q R A L H F A I S E Y N (SEQ ID NO:1)

or be significantly homologous thereto.

Any member of the Cystatin family may be used.

The invention also provides a cDNA sequence for the expression of Cystatin or a similar peptide.

The amino-acid sequence of Cystatin (SEQ ID NO:2) is shown in FIG. 1.

The invention further provides use of a Cystatin type peptide or a natural or synthetic similar peptide in the preparation of a medicament for the treatment or prevention of periodontal disease.

The invention further provides the use of a nucleic acid sequence which encodes a Cystatin type peptide in the preparation of a medicament for the treatment or prevention of periodontal disease.

The basis for the present invention will be illustrated with reference to the following experiments.

Experiment 1

Relationship Between Saliva from Migraine Sufferers and Lack of Periodontal Disease.

Antibacterial Activity of Saliva from Migraine Sufferers.

TABLE 1

| Saliva dilution | Source - non-migraine sufferer | | | Migraine Sufferer | | |
|---|---|---|---|---|---|---|
| in water | B. frag | P. Ging | P. Int | B. frag | P. Ging | P. Int |
| 1 | H | N | N | H | N | N |
| 0.5 | H | N | S | H | N | S |
| 0.25 | H | N | M | H | N | M |
| 0.125 | H | H | H | H | N | M |
| 0.0625 | H | H | H | H | M | M |
| 0.03125 | H | H | H | H | M | M |

TABLE 1-continued

| Saliva dilution | Source - non-migraine sufferer | | | Migraine Sufferer | | |
|---|---|---|---|---|---|---|
| in water | B. frag | P. Ging | P. Int | B. frag | P. Ging | P. Int |
| 0 Control | H | H | H | H | H | H |
| No bacteria Control | N | N | N | N | N | N |

H = high levels of bacteria
M = medium levels
S = small level
N = no bacteria
B. Frag = Bacteriodes fragilis
P. Ging = Porphyromonas gingivalis
P. Int = Porphyromonas intermedius Microtitre wells were inoculated with $5 \times 10^4$ bacteria per well in 1 ml of media. 100 µl of nondiluted/diluted saliva was added as set out in the table. Wells were monitored after 48 hours for presence of bacterial growth.

Saliva from migraine sufferers did not appear to have an inhibitory effect on *Bacteriodes fragilis* but had a significant inhibitory effect on *Porphyromonas gingivalis* and *Porphyromonas intermedius*.

Experiment 2

The Relationship Between Periodontal Disease and Migraine.

Prior to this study little was known about the relationship between periodontal disease and migraine. The clinical impression observed by the present inventors was that significant periodontal disease was an uncommon finding in patients referred for management of migraine.

Materials and Methods

Subjects who had been diagnosed as having migraine were identified from the computerised diagnostic database of patients referred to the Oral Medicine Clinic, School of Dentistry, Queen's University, Belfast. All subjects were free of medical conditions or drug therapies known to have an effect on the periodontium. In this study available radiographs were used and measurements of bone loss were made only on sites displaying clear and complete images of the teeth. Orthopantomographs were taken with Dupont Ultrafilm using one of three units OPG5 (Siemens, Bensheim, Germany), by one of two senior radiographers both of who had been trained at the School of Dentistry, Belfast. These radiographs were processed in a standard manner using a Durr-Dental AC245L processor (Siemens, Bensheim, Germany), Orthoceph (Planmeca, Finland) or Siemens Orthophos plus (Siemens, Bensheim Germany). Films were developed with a Agfa-Gevaert Curix 242S (Agfa, Leverkusen, Germany) processor.

Assessment of Radiographs

One investigator examined all the films blinded to the clinical details of the subjects. Radiographs were examined under standard conditions of lighting, using an illuminated light box and 5× magnification. Alveolar bone levels on the mesial and distal aspects of each tooth, excluding third molars, were evaluated from the available radiographs and the percentage alveolar bone loss was recorded. The methodology has been previously described by (Mullally & Linden 1996). Bone loss was assessed as a percentage of the expected bone height, calculated to the nearest 10%, using a modification of the 5 point Schei ruler. Where there was any doubt a surface was assigned the lower value for bone loss. Each tooth was represented by the score for the worst affected surface. Third molars were excluded from the analysis.

Calibration and Reproducibility

There was a period of training during which guidelines were developed and as part of the definitive study measurement reproducibility was assessed. To ensure that bone loss was consistently measured 9 randomly selected radiographs were re-measured. There was exact correspondence of the original and repeated measurement for 81% of teeth examined. A further 17% of scores were within 10% and the remaining 2% of scores within 20% of the original bone loss measurement. This indicated that the reproducibility of this method of assessing proximal alveolar bone loss was within acceptable limits.

Results

The study group (n=60) consisted of three groups of subjects, twenty with a diagnosis of migraine, twenty with a diagnosis of toothwear and twenty controls with neither migraine nor toothwear. All subjects were non-smokers free from medical conditions or drug therapy known to have an effect on the periodontium and the three groups were well matched for age and gender. The details of the three groups are described in Table 2. The distribution of males to females in the tooth wear group was 3:1. This was different to the migraine or control group in which females were predominant.

The mean score for bone loss for the migraine group was 9.6 (S.D. 6.4) which was statistically significantly lower than that for either the toothwear 14.4 (S.D. 6.1; p=0.037) or the control group 13.8 (S.D. 5.9; p=0.022).

Discussion

Based upon a radiographic analysis of proximal alveolar bone height in sixty subjects recruited from hospital clinics our results suggest that the severity of periodontitis is significantly less in migraineurs than in either age and gender matched healthy controls or individuals with toothwear.

The limitations of this study include the fact that the clinical diagnosis of migraine or toothwear was made by a number of clinicians who were not directly involved in the study and the specific criteria for each diagnosis may exhibit some inter-examiner variation. Controls were recruited from the Admissions Clinic in the School of Dentistry on the basis that they did not give a history of migraine at that time. The distribution of males to females was different in the toothwear group compared with the migraineurs and controls, however this reflects the prevalence of toothwear in these clinics.

Overall the bone loss experienced by all three groups were relatively low for their age however the significantly lower values in the migraine group compared with controls would merit further investigation to investigate the relationship between migraine and periodontal disease. The fact that a significant difference was evident in such small groups may be indicative of a relationship between migraine and periodontal disease. These data support the suggestion that migraine has a putative protective effect on the periodontium. One possibility was that neuropeptides which mediate changes found in migraine may spill over into the mouth. It was speculated that Substance P and Neurokinin A, which are released during a migraine attack had a role in protecting against alveolar bone loss.

It is concluded from this radiographic study that migraineurs have less alveolar bone loss than subjects with toothwear or healthy controls.

TABLE 2

Age and gender distribution of study population

| Status | Number | Mean Age | Males | Females |
|---|---|---|---|---|
| Controls | 20 | 51.7 (8.5) | 8 | 12 |
| Migraine | 20 | 47.6 (10.8) | 7 | 13 |
| Toothwear | 20 | 50.2 (9.3) | 15 | 5 |

Experiment 3

The present inventors used Substance P antisera initially to determine the levels of Substance P in saliva from migraineurs. Remarkably high levels were observed and suggested that the antibody was cross-reacting with another/other peptide(s). HPLC separation was carried out and fractions were dot blotted and reacted with Substance P antisera. Reacting fractions were further purified and sequenced. The sequence of the significantly reacting peptide was found to correspond to the peptide sequence of Cystatin SN. Further analysis indicated that the levels of Cystatin SN are about ten times higher in migraineurs than non-migraineurs.

Experiment 4

Triggering Migraine Attacks

The molecular basis of migraine was previously unknown. Work by the inventors in this area began with the clinical observation that most migraineurs woke with a migraine from sleep. This casts considerable doubt on the previously described relationship between migraine and so called trigger factors such as the ingestion of cheese, chocolate, citrus fruits and red wine for two reasons: firstly, the time scale was too long as patients normally sleep for 6-8 hours and yet the pharmacological effects of an ingredient of these substances should produce an effect within 1-2 hours and secondly, critical evaluation of the evidence for these factors actually triggering true migraine is weak.

In view of these observations, investigations were carried out regarding factors during sleep which could conceivably trigger attacks of migraine. The resulting research identified tooth clenching as the major problem and this led to an appliance being devised which obviated tooth clenching during sleep and in turn prevented attacks of migraine. Indeed following one year of treatment with such a device, around 85% of migraineurs suffered no further attacks.

Whilst deciding on how long a patient had to wear the appliance in order to permanently alleviate their migraine, it became clear that a three month period was too short. Indeed all patients who discontinued their attacks in that time will experience an attack of migraine within ten days of stopping appliance therapy. In essence the appliance could therefore be used as a mechanism to trigger migraine in those individuals.

By having a model to trigger migraine attacks, the constituents of saliva were analysed and this led to the identification of a peptide which shows two main features. Firstly the level of this peptide is about ten times higher in migraineurs than non-migraineurs and secondly levels rose markedly in the 24 hours before a migraine attack. This peptide was isolated and sequenced and the sequence was shown to correspond with the known sequence of Cystatin SN.

General Discussion

The present inventors have surprisingly found that one feature of migraineurs which makes them clinically different from non-migraineurs is their apparent lack of periodontal disease. Bone loss levels have been studied by means of radiography in migraineurs and non-migraineurs and this has shown that migraineurs have less periodontal disease than non-migraineurs. These findings are probably not due to the excessive forces exerted on the teeth during clenching as there are other disorders such as temporomandibular joint dysfunction disorders in which patients also exhibit excessive force on their teeth, but they appear to have a normal level of periodontal disease, and as such the inventors propose that the infrequent occurrence of periodontal disease in migraineurs is due to the increased levels of the peptide Cystatin SN.

The World Health Organisation recognises that there are a number of individuals who are apparently "immune to periodontal disease". This figure is put at around 10% which interestingly from an epidemiological point of view is about the same proportion of population who suffer from migraine.

It can be concluded that in the course of evaluating individuals who are susceptible and non-susceptible to periodontal disease, that factors in their medical history such as migraine are likely to have been ignored as not being relevant but in light of the conclusions drawn herein, they are clearly relevant. The anti-microbial effect of Cystatin SN is thus believed to be central to the prevention of periodontal disease in these individuals.

Although the inventors do not wish to be bound by any specific theorem, the effect of Cystatin SN has been investigated in relation to its anti-microbial effect on periodontal pathogens, but Cystatin SN is also a profound vasodilatory agent and this may be responsible for enhancing the host response towards putative periodontal pathogens.

The present invention provides evidence that Cystatin SN can be incorporated into dentifrice and is expected to have an effect on gingivitis and periodontal disease. Modern molecular and cloning techniques will enable large amounts of Cystatin SN to be produced and therefore an evaluation of its clinical effects in respect of preventing periodontal disease to be studied.

Potential studies looking at the effectiveness of Cystatin at preventing infection which leads to periodontal disease can be evaluated through carrying out studies on a group of individuals who are known to be biochemically different from migraineurs. This experimental technique wherein a migraineur specific characteristic is identified and given to non-migraineurs is likely to lead to results which would indicate whether the raised levels of Cystatin SN in migraineurs explains the associated decrease in susceptibility to periodontal disease.

Clinical trials involving clinical evaluation of gingivitis and periodontitis and radiographic evaluation coupled with studies of the release of Cystatin SN in vivo and in vitro from dentifrice preparations can be carried out.

The invention claimed is:

1. A method of treating a subject having a periodontal disease comprising the step of administering a peptide to the subject in need of such treatment, wherein said peptide comprises the amino acid sequence Ile-Ile-Pro-Gly-Gly-Ile-Tyr-Asn-Ala-Asp-Leu-Asn-Asp-Glu-Trp-Val-Gln-Arg-Ala-Leu-His-Phe-Ala-Ile-Ser-Glu-Tyr-Asn (SEQ ID NO:1).

2. The method of treating a subject having periodontal disease as claimed in claim 1 wherein said peptide is SEQ ID NO:2.

* * * * *